United States Patent [19]
Honeyager et al.

[11] Patent Number: 6,111,501
[45] Date of Patent: Aug. 29, 2000

[54] HAND-HELD ENVIRONMENTAL MONITOR

[75] Inventors: Kevin S. Honeyager; Terrie L. McDaniel; Larry D. Canady, all of San Antonio, Tex.

[73] Assignee: Southwest Research Institute, San Antonio, Tex.

[21] Appl. No.: 09/339,593

[22] Filed: Jun. 24, 1999

Related U.S. Application Data

[60] Provisional application No. 60/091,007, Jun. 25, 1998.

[51] Int. Cl.$^7$ .................................................. G08B 19/00
[52] U.S. Cl. ........................................... 340/521; 600/301
[58] Field of Search ............................. 340/573.1, 573.3, 340/601, 576, 521; 128/630, 745, 746; 600/301; 73/336.5

[56] References Cited

U.S. PATENT DOCUMENTS

| | | | |
|---|---|---|---|
| 4,276,888 | 7/1981 | Smith et al. | 128/706 |
| 4,592,661 | 6/1986 | Wilson | 374/10 |
| 4,869,874 | 9/1989 | Falat | 422/53 |
| 5,055,267 | 10/1991 | Burroughs et al. | 422/83 |
| 5,140,519 | 8/1992 | Friesdorf et al. | 364/413.03 |
| 5,682,882 | 11/1997 | Lieberman | 128/630 |
| 5,917,414 | 6/1999 | Oppelt et al. | 340/573.1 |
| 5,920,827 | 7/1999 | Baer et al. | 70/3 |

OTHER PUBLICATIONS

Search Report for PCT/US/14280 mailed Sep. 14, 1999, 7 pages.

*Primary Examiner*—Jeffery A. Hofsass
*Assistant Examiner*—Hung Nguyen
*Attorney, Agent, or Firm*—Baker Botts L.L.P.

[57] ABSTRACT

A hand-held monitor (10) for monitoring environmental or physiological conditions affecting the user. The monitor (10) has a main housing (10a) and a sensor module (10b). The sensor module (10b) has a plurality of sensors (33–36) extending from it. The sensor module (10b) is generally cylindrical in shape and rests in a curved cradle (14c) of the main housing (10a). This permits the sensor module (10b) to rotate between a position in which the sensors are deployed and extend outwardly from the main housing (10a), and a position in which the sensors rest in the main housing (10a). The main housing (10a) contains processor-based electronics circuitry (50) for processing the data acquired by the sensors. The sensor module (10b) contains sensor electronics circuitry (60), including all circuitry unique to the sensors, and is easily detachable from the main housing (10a). This permits sensor modules having the same or different sensors to be easily interchanged.

22 Claims, 5 Drawing Sheets

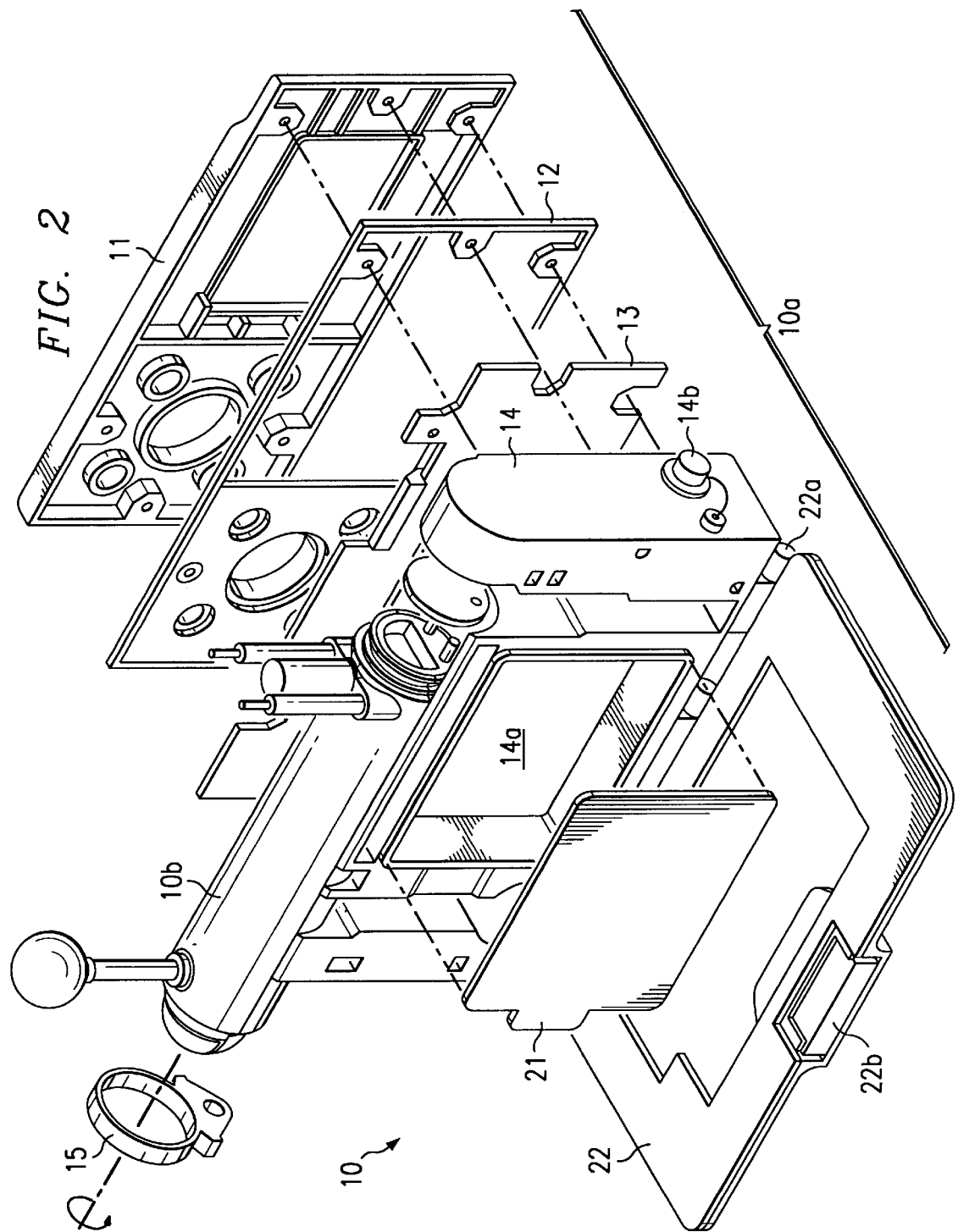

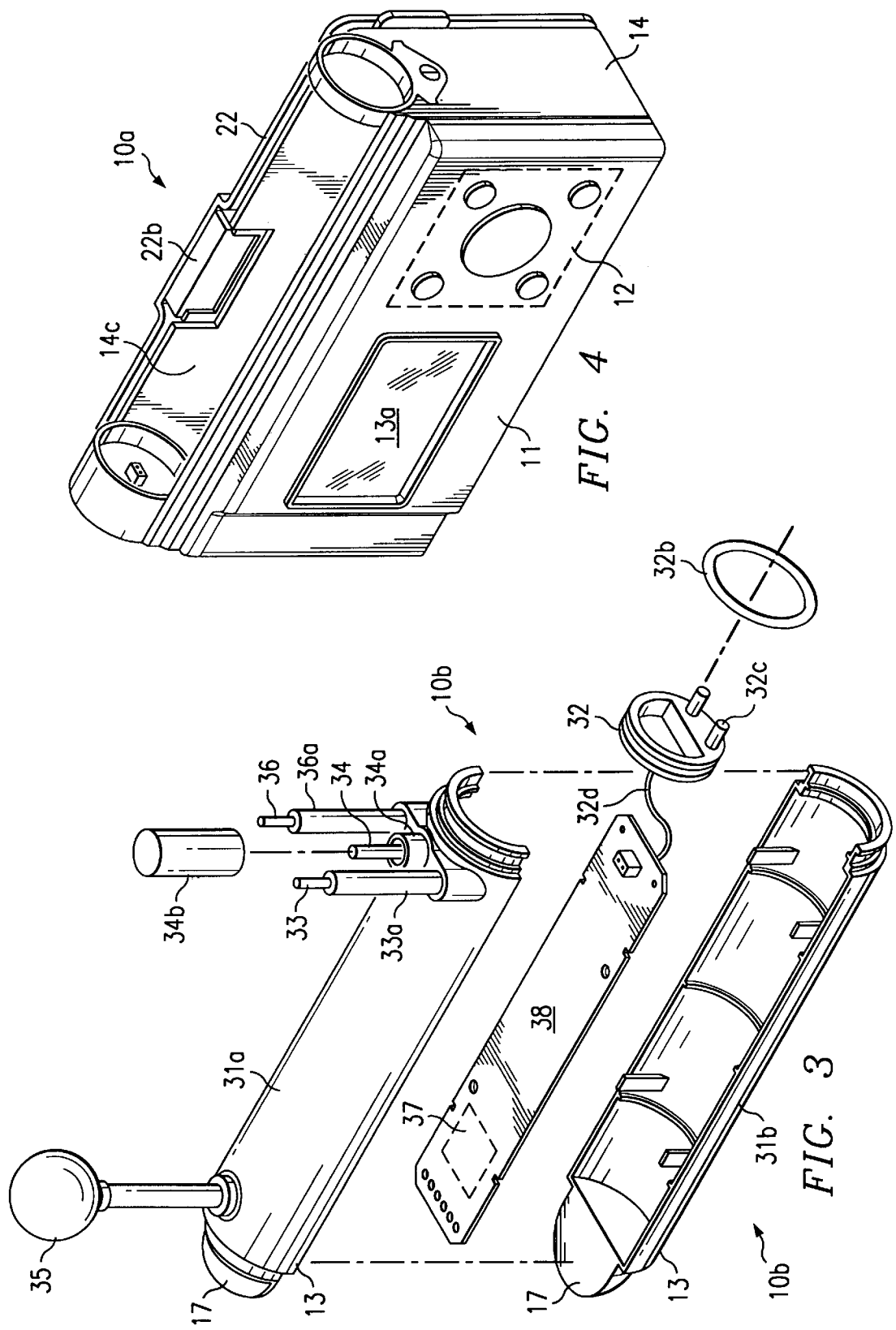

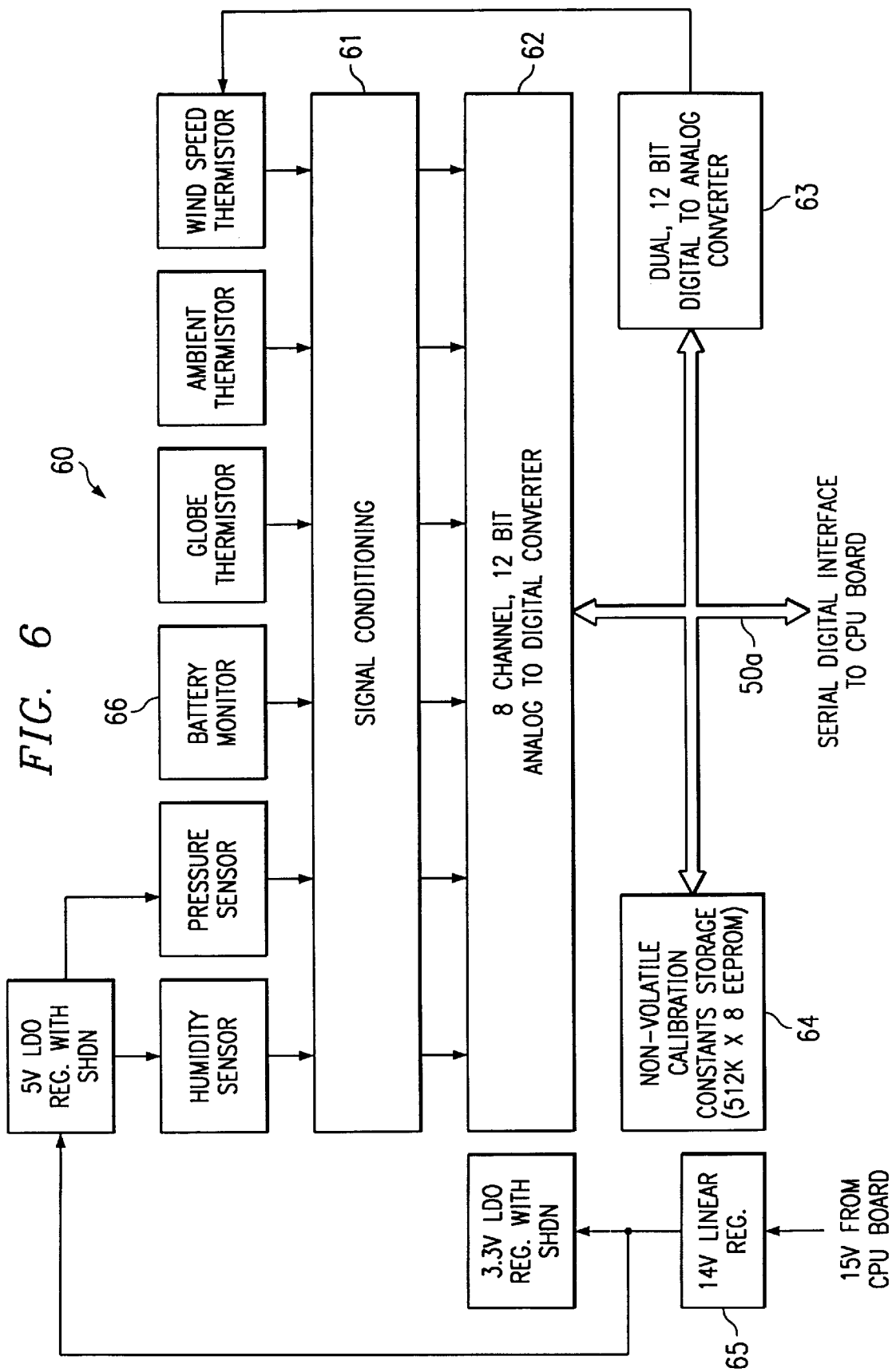

HAND-HELD ENVIRONMENTAL MONITOR

RELATED PATENT APPLICATION

This application claims the benefit of U.S. Provisional Application No. 60/091,007, filed Jun. 25, 1998 and entitled "Hand-Held Environmental Heat Stress Monitor".

GOVERNMENTAL RIGHTS

The U.S. Government has a license in this invention and the right in limited circumstances to require the patent owner to license others on reasonable terms as provided for in Contract No. SWR-94-RY-13 awarded by United States Air Force Research Laboratory through Synectics Corporation.

TECHNICAL FIELD OF THE INVENTION

The present invention relates generally to the field of data acquisition systems, and particularly to a portable environmental data monitor that can be used to monitor environmental conditions affecting workers.

BACKGROUND OF THE INVENTION

In occupations or activities which occur under extreme environmental conditions, such as high heat and/or humidity, it is often necessary to monitor the environment to determine if working conditions are safe. The environmental parameters which are typically measured are dry bulb, wet bulb, and black globe temperature. From these three parameters, the wet bulb globe temperature (WBGT) index can be calculated. The WBGT index is an industry standard metric for assessing susceptibility to heat strain. There are a number of commercially available devices which calculate the WBGT index, and some devices suggest a maximum safe work time based on this result.

In the field of environmental monitoring it is desirable to have a portable measurement device so that measurements can easily be taken in different locations. Previous monitoring devices have sensors that are mounted to a tripod and attached to a separate display unit by a cable. This can limit their use to areas which can physically accommodate such equipment. Other devices use individual sensors which directly attach to the display unit, and are removed and placed in a protective case for storage.

SUMMARY OF THE INVENTION

One aspect of the invention is a portable stress monitor for monitoring conditions under which physiological activity is occurring. The conditions monitored may be environmental, such as ambient temperature and humidity, or physiological, such as heart rate or body temperature. A main housing has a front piece and a rear cover. A curved cradle at the surface of the main body holds a sensor module. The sensor module rests in the curved cradle, and has a generally cylindrical shape such that it is rotatable within the curved cradle from a sensor deployed position to a sensor storage position. One or more sensors are attached to the sensor module, each sensor mounted on a mast, such that the sensors extend outwardly from the main body when the sensor module is in the deployed position and rest in the main body when the sensor module is in the storage position. A main electronics circuit is contained within the main body, and is operable to process data acquired by the sensors. A sensor electronics circuit is contained within the sensor module, and is operable to perform sensor-related functions, such as signal conditioning and A/D conversion. A display is attached to the outer surface of the main body for providing read out information, and a keypad receives input from the user.

An advantage of the heat/stress monitor is that it is conveniently portable and provides protection for the sensors when the device is not in use. It does not require any assembly for use or storage. It is capable of determining work/rest cycles and water requirements, to prevent workers from having unhealthy reactions to environmental conditions. The device acquires data from various sensors, including wind speed, and this data is incorporated into a predictive model.

BRIEF DESCRIPTION OF THE DRAWINGS

FIG. 2 is a perspective rear view of the stress monitor of FIG. 1.

FIG. 3 is a perspective view of the sensor module of FIGS. 1 and 2.

FIG. 4 is a perspective front view of the assembled main body of FIGS. 1 and 2.

FIG. 6 is a block diagram of the sensor electronics contained within the sensor module.

DETAILED DESCRIPTION OF THE INVENTION

Housing and Structure

Figure 1:
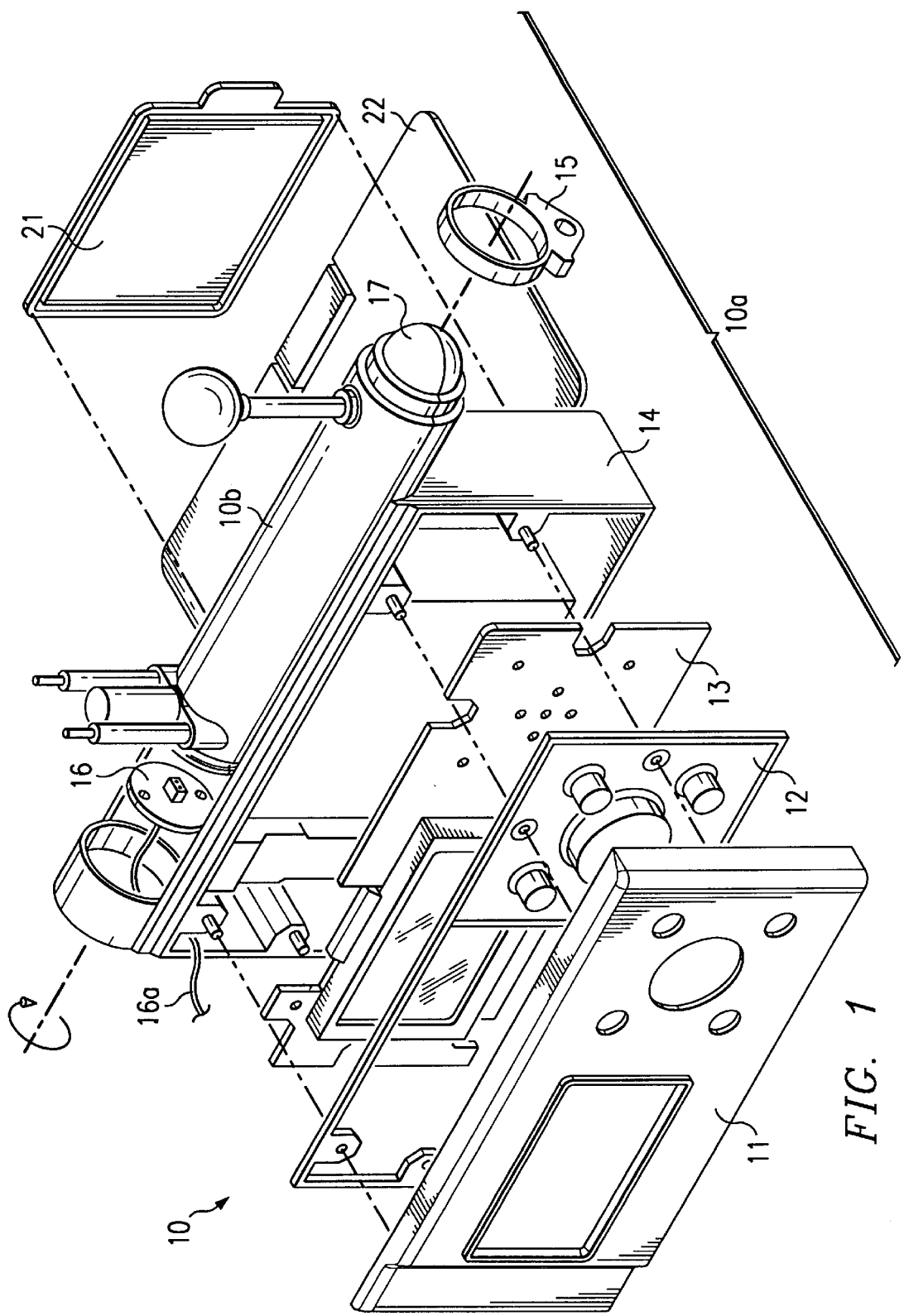
FIG. 1 is a perspective front view of the stress monitor, with the sensor module in the "deployed" position.

FIGS. 1 and 2 are exploded front and rear views of an environmental data monitor 10 in accordance with the invention, respectively. In the example of this description, monitor 10 is adapted for use in monitoring environmental conditions associated with heat stress, and has sensors and programming appropriate for that application. However, monitor 10 could be easily adapted for monitoring other environmental conditions, such as cold, air quality, and noise. Appropriate sensors could be added or substituted for those described herein.

Structurally, monitor 10 is comprised of a main body 10a and a sensor module 10b. In FIGS. 1 and 2, sensor module 10b is in the "deployed" position, positioned for operation of its sensors. A hinged rear cover 22 of main body 10a is open, but could be closed to protect the sensors of sensor module 10b during use.

The main body 10a of monitor 10 has a front piece 11, a keypad 12, a CPU board 13, with a midpiece 14, a battery cover 21, a rear cover 22 with latch 22a, an endpiece 15, and a sensor module connector 16.

CPU board 13 is located between front piece 11 and midpiece 14. On its front side, CPU board 13 contains the graphics display and traces for keypad 12. Other electronic components are on the rear side. The electrical circuitry of CPU board 13 is explained below in connection with FIG. 5.

Midpiece 14 has a curved sensor bed 14c at its top end. As explained below, sensor bed 14c, such that sensor module 10b may rotate at least 180 degrees. FIG. 2 illustrates this rotation.

Sensor module connector 16 attaches to midpiece 14, such as by screws. The attachment is after its wiring harness 16a is threaded to CPU board 13. Sensor module connector 16 has alignment holes 16b, which prevent a rotating connector 32 on sensor module 10b from making contact with sensor module connector 16 until it is properly aligned.

A battery compartment 14a in midpiece 14 contains four AA-size batteries wired in series to provide a nominal six volt DC power source. A battery cover 21 is a friction fit rubber cover, which seals the battery compartment 14a when rear cover 22 is closed.

The '+' and '−' terminals of the batteries protrude through the battery compartment 14a and a wiring harness connects them to CPU board 13. An external connector 14b also attaches to CPU board 13 with a wiring harness. All wiring harnesses are of sufficient length to allow CPU board 13 to be removed from the midpiece 14 and manipulated for repair.

Once all wiring harnesses are attached to the CPU board 13, keypad 12 is placed into the front piece 11. Keypad 12 is made from conductive rubber and forms a weatherproof seal where it comes in contact with the midpiece 14. The front piece 11 attaches to the midpiece 14 by screws that enter through the rear of the midpiece 14.

Rear cover 22 and midpiece 14 have a hinge-type attachment 22a along their bottom edges. A sliding latch 22b is attached to the rear cover 22 by compression springs, which hold latch 22b in its latched position. The rear cover 22 is opened by operating the latch 22b. A compressible gasket may be attached to the perimeter of the rear cover 22 to serve as a seal and to allow the rear cover 22 to spring out from the midpiece 14 when unlatched.

Sensor module 10b is cylindrical in shape, with a rotating connector 32 at one end and a rotation knob 17 at the other. Connector 32 permits sensor module 10b to rotate within the sensor bed 14c of midpiece 14.

When monitor 10 is in the "storage" position (not shown), sensor module 10b is rotated approximately 180 degrees from the "deployed" position illustrated in FIGS. 1 and 2. This permits its sensors to be placed under rear cover 22, when cover 22 is hinged shut.

For assembly, sensor module 10b is slid into position on the main body 10a with the sensors in their deployed position and the rear cover 22 unlatched. Once the sensor module 10b is seated properly, endpiece 15 is positioned over the knob 17 and attached to the midpiece 14 with screws. For the storage position of monitor 10, the sensors can be rotated into the sensor cavities in the midpiece 14, and the rear cover 22 can be closed.

FIG. 3 illustrates sensor module 10b in further detail. A feature of the invention is that monitor 10 easily permits sensor modules 10b to be interchanged and used with the main body 10a. All signal processing and calibration information is stored in the sensor module 10b, with a digital control interface to the main body 10a.

Sensor module 10b is comprised of a cylindrical housing 31, having an upper half 31a and a lower half 31b. The two parts of housing 31 are screwed together, ultrasonically welded, glued, or otherwise attached.

The upper half 31a provides a platform for various sensors. In the embodiment of FIG. 3, sensor module 10b has a dry bulb sensor 33, relative humidity sensor 34, black globe sensor 35, and wind speed sensor 36. Thus, monitor 10 has three thermistors: dry bulb, black globe, and wind speed. Wet bulb globe temperature (WBGT) is obtained by measuring relative humidity with sensor 34 and the dry bulb temperature with sensor 33 and using a mathematical formula to determine wet bulb temperature. Alternatively, a dedicated wet bulb sensor could be used.

The dry bulb sensor 33, globe sensor 35, and wind speed sensor 36 are each located on a mast 33a, 35a, and 36a. These masts protrude perpendicular to the face of the cylindrical housing 31. A removable light-shadowing housing 34b covers the humidity sensor 34.

Sensor PCB (printed circuit board) 38 is contained within sensor housing 31, between upper half 31a and the lower half 31b. Sensor PCB 38 contains the sensor electronics 50, described below in connection with FIG. 6.

An atmospheric pressure sensor 37 is located inside sensor module 10b. In the embodiment of FIG. 3, pressure sensor 37 is mounted on the underside of sensor PCB 38.

At one end of sensor module 10b is a rotating connector 32, which has a groove on its edge to allow it to rotate within cylindrical housing 31. The upper half 31a and lower half 31b of housing 31 have mating ridges. An O-ring 32b is slipped onto the cylindrical housing 31.

When rotating connector 32 is plugged into fixed connector 16, there is a seated rotating connection between sensor module 10b and main body 10a. As a result of the rotating connector 32 and O-ring 32b, sensor module 10b is sealed from the effects of the environment. Alignment pins 32c provide strain relief for the connector pins and sockets when sensor module 10b is rotated.

Referring again to FIGS. 1 and 2, main body 10a has cavities into which the various sensors fit when sensor module 10b is rotated approximately 180 degrees into a "storage" position. The arrow is FIG. 2 illustrates the direction of rotation. The hinged rear cover 22 is closed to protect the sensors when they are stored. Cover 22 can also be re-closed after it is opened and the sensors are deployed into their "operate" position.

As stated above in connection with FIGS. 1 and 2, and as also illustrated in FIG. 4, main body 10a has an endpiece 15. The endpiece 15 fits over a rotation knob 17 on sensor module 10b. It attaches to main body 10a and holds sensor module 10b in place. Endpiece 15 may be removed to permit sensor module 10b to be removed, such as for replacement or repair.

Discrete wires 32d from the rotating connector 32 are attached to the sensor PCB 38. When the assembled sensor module 10b is attached to the main body 10a, rotating connector 32 is held in a fixed position with respect to the main body 10a by a mated connection. When the knob 17 is used to rotate the sensor module 10b, the upper half 31a, lower half 31b, and sensor PCB 38 rotate around the rotating connector 32.

Electronics Circuitry

Figure 5:
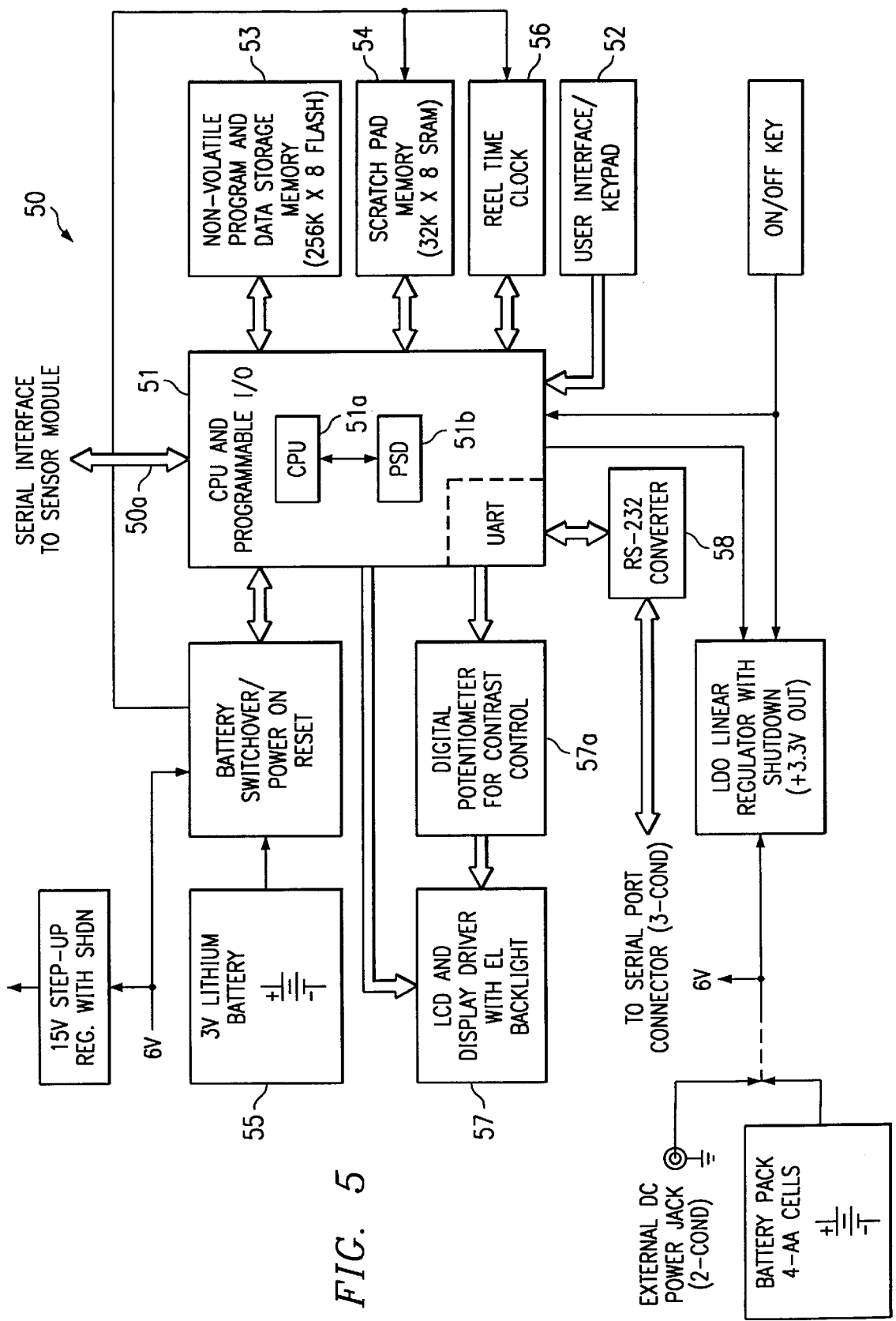
FIG. 5 is a block diagram of the main electronics contained within the main body.

FIGS. 5 and 6 are functional block diagrams of the electronics of the present invention. FIG. 5 illustrates the main electronics 50 contained within main body 10a. FIG. 6 illustrates the sensor electronics 60 contained within sensor module 10b. A serial digital interface 50a provides the electrical connection between main electronics 50 and sensor electronics 60.

Main electronics 50 has a central processing unit (CPU) 51a with a peripheral system device (PSD) 51b. The PSD 51b provides address decode logic, additional static RAM and digital I/O ports, and a bootloader routine for the flash memory 53. A static RAM 54 provides both scratchpad memory and nonvolatile storage for data logging applications. RAM 54 is backed up by a lithium battery 55. The lithium battery 55 also maintains a real time clock 56, which can be used for timestamping logged data. The graphics display 57 is addressed by the CPU 51a and uses a digital potentiometer 57a for contrast adjustment. The backlight control for the graphics display 57 is controlled by the PSD 51b. The keypad 52 is interfaced to digital I/O ports on the PSD 51b.

The system is powered by a DC power source, which may be either user-replaceable batteries placed in compartment 14a or an external power source.

An RS-232 converter 58 converts the TTL-level signals on the CPU board 10 to RS-232 signals for the external serial connector.

The main body 10*a* of monitor 10 functions as an intelligent user interface containing the graphics display, keypad, power supply CPU and associated digital electronics. The main body also contains an external port which can be used to supply external power and communicate with a personal computer through an RS-232 interface. Software can also be loaded into the device through this port and stored in flash memory.

The connection between main body 10*a* and sensor module 10*b* provides battery power, supply voltage, and a digital control interface. All sensing electronics and storage for calibration and sensor identification information is located on the sensor module 10*b*. This allows sensor module 10*b* to be calibrated independently of the main body 10*a* and to produce the same results when attached to any main body 10*a*.

The design of monitor 10 permits different types of sensor modules to be used with the main body, whereby the sensor module 10*b* can be queried by the main body 10*a* to determine the type of each sensor and its calibration information. The application software in the main body 10*a* can then configure itself to acquire and display the sensor data. Alternatively, a dedicated application for a given type of sensor module 10*b* can be loaded into the flash memory 53 through an external port.

Referring to FIG. 6, the sensor electronics 60 contains signal conditioning circuitry for the dry bulb sensor 33, the black globe sensor 35, the relative humidity sensor 34, the wind speed sensor 36, and the pressure sensor 37.

The analog voltages produced by the various sensors are digitized by the A/D converter 62. A D/A converter 63 is used to provide current to the wind speed sensor 36 and to heat it to a constant temperature above the dry bulb temperature. The amount of power required to heat the wind speed sensor 36 is related to the wind speed.

An EEPROM 64 stores all calibration information related to the sensors 33–37. The calibration information may include various calibration constants, unique to each sensor. In general, all circuitry and programming unique to any sensor is placed on sensor module 10*b* rather than in main body 10*a* so that sensor modules having the same, or different, sensors may be easily interchanged.

A/D converter 62, D/A converter 63, and EEPROM 64 all share the same serial control lines on the interface 50*a*, with the exception of their chip select signals. This minimizes the number of connections that need to be made between the CPU electronics 50 and the sensor electronics 60.

Voltage regulator 65 produces a stepped-up voltage for the sensor electronics 60. The battery voltage is delivered to the sensor electronics 60, where it is input to a battery monitor 66, whose output signal is converted to digital form by A/D converter 62, and delivered back to the CPU electronics 60. The location of battery monitor 66 in sensor electronics 60 is merely for convenience of using A/D converter 62, and in other embodiments, battery monitor 66 could be part of CPU electronics 50.

Data Processing

CPU 51*a* can be programmed to execute various environmental data processing algorithms. For example, when monitor 10 is used to heat stress monitoring, known heat strain models can be used. For example, a model based on the WBGT index may be used.

A feature of the invention is the incorporation of wind speed into heat strain models. As a result, the effect of evaporative cooling is considered in determining weather effects.

Measured parameter data acquired from sensor module 10*b* can be combined with user input parameter data acquired via keypad 12 or other means. Such parameters might include, clothing type, work type, or work rate.

As stated above, monitor 10 can be easily adapted for use with other or additional sensors. For example, one sensor might be an air quality sensor, such as one that measures oxygen content or one or more pollutants. Or, a sensor might measure noise. Other sensors might measure the user's physiological conditions, such as heart rate, blood pressure, or body temperature (skin or core). For physiological monitoring, sensors such as used by athletes could be used—for example, a heart rate monitor that attaches to the user's finger and provides input to the A/D converter 62 of sensor module 10*b* or directly to the processor 51 of the main body 10*a*.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A portable monitor for monitoring conditions in which physiological activity occurs, comprising:

a main housing having a front piece and a rear cover, the housing having a curved cradle at its surface;

a sensor module that rests in the curved cradle and has a generally cylindrical shape, such that it is rotatable within the curved cradle from a sensor deployed position to a sensor storage position;

a plurality of sensors attached to the sensor module, each sensor mounted on a mast, such that the sensors may extend outwardly from the main housing when the sensor module is in the deployed position and may rest in the main housing when the sensor module is in the storage position;

a main electronics circuit contained within the main housing, operable to process data acquired by the sensors;

a sensor electronics circuit contained within the sensor module;

a display viewable at the outer surface of the main housing for providing read out information; and a keypad for receiving input from a user.

2. The monitor of claim 1, wherein the sensors include an ambient temperature sensor and a humidity sensor.

3. The monitor of claim 1, wherein the sensors include a black globe sensor.

4. The monitor of claim 1, wherein the sensors include a wind speed sensor.

5. The monitor of claim 1, further comprising an atmospheric pressure sensor within the sensor module.

6. The monitor of claim 1, wherein the main electronics circuit has a processor programmed in accordance with a heat stress model.

7. The monitor of claim 1, wherein the model incorporates wind speed parameters, and wherein the sensors include a wind speed sensor.

8. The monitor of claim 1, wherein the sensor electronics has all electronics unique to the sensors.

9. The monitor of claim 1, further comprising a single data interface connecting the main electronics circuit and the sensor electronics circuit.

10. The monitor of claim 1, wherein the sensors include a heart rate sensor.

11. The monitor of claim 1, wherein the sensors include a blood pressure sensor.

12. The monitor of claim 1, wherein the sensors include a body temperature sensor.

13. The monitor of claim 1, wherein the rear cover covers the sensors in the closed position and opens to permits the sensor module to be rotated to the deployed position.

14. The monitor of claim 1, wherein the sensor electronics circuit has all electronics unique to the sensors.

15. The monitor of claim 1, wherein the main electronics circuit has all circuitry common to the sensors.

16. The monitor of claim 1, wherein the main electronics circuit is further operable to process additional parameters input by a user.

17. The monitor of claim 1, wherein the sensor module is removably attached to the main housing at one end of the sensor module.

18. The monitor of claim 1, wherein the main housing has a midpiece between the front piece and rear cover, the midpiece having the curved cradle at its upper surface.

19. A portable environmental heat stress monitor, comprising:
- a main housing having a front piece and a rear cover, the main housing having a curved cradle at its surface;
- a sensor module that rests in the curved cradle and has a generally cylindrical shape, such that it is rotatable within the curved cradle from a sensor deployed position to a sensor storage position;
- a plurality of sensors attached to the sensor module, each sensor mounted on a mast, such that the sensors extend outwardly from the main housing when the sensor module is in the deployed position and rest in the main housing when the sensor module is in the storage position, the sensors including at least a dry bulb temperature sensor;
- a main electronics circuit contained within the main housing, operable to process data acquired by the sensors and to provide heat stress data output;
- a sensor electronics circuit contained within the sensor module;
- a display viewable at the outer surface of the main housing for providing read out information; and
- a keypad for receiving input from a user.

20. A portable environmental heat stress monitor, comprising:
- a main housing having a front piece and a rear cover;
- a sensor module operable to move from a sensor deployed position to a sensor storage position;
- a plurality of sensors attached to the sensor module, each sensor mounted on a mast, such that the sensors extend outwardly from the main housing when the sensor module is in the deployed position and rest in the main housing when the sensor module is in the storage position, the sensors including at least a humidity sensor and a wind speed sensor;
- a main electronics circuit contained within the main housing, operable to process data acquired by the sensors and to provide heat stress data output that incorporates wind speed as a parameter;
- a sensor electronics circuit contained within the sensor module;
- a display viewable at the outer surface of the main housing for providing read out information; and
- a keypad for receiving input from a user.

21. The monitor of claim 20, wherein the main housing has a curved cradle at its surface and wherein the sensor module rests in the curved cradle and is rotable in the curved cradle between the deployed position and the storage position.

22. A portable physiological monitor, comprising:
- a main housing having a front piece and a rear cover, the main housing having a curved cradle at its surface;
- a sensor module that rests in the curved cradle and has a generally cylindrical shape, such that it is rotatable within the curved cradle from a sensor deployed position to a sensor storage position;
- a plurality of sensors attached to the sensor module, each sensor mounted on a mast, such that the sensors extend outwardly from the main housing when the sensor module is in the deployed position and rest in the main housing when the sensor module is in the storage position, the sensors including at least a body temperature sensor;
- a main electronics circuit contained within the main housing, operable to process data acquired by the sensors and to provide physiological data;
- a sensor electronics circuit contained within the sensor module;
- a display viewable at the outer surface of the main housing for providing read out information; and
- a keypad for receiving input from a user.

* * * * *